United States Patent
Chen et al.

(10) Patent No.: US 11,512,333 B2
(45) Date of Patent: Nov. 29, 2022

(54) **METHOD FOR PRODUCING TETRAHYDROPYRIMIDINE BY FERMENTING RECOMBINANT *CORYNEBACTERIUM GLUTAMICUM***

(71) Applicant: Beijing KansenBio Technology Ltd., Beijing (CN)

(72) Inventors: Zhen Chen, Beijing (CN); Dehua Liu, Beijing (CN)

(73) Assignee: Beijing KansenBio Technology Ltd., Beijing (CN)

( * ) Notice: Subject to any disclaimer, the term of this patent is extended or adjusted under 35 U.S.C. 154(b) by 0 days.

(21) Appl. No.: 16/612,692

(22) PCT Filed: Nov. 30, 2017

(86) PCT No.: PCT/CN2017/113806
§ 371 (c)(1),
(2) Date: Mar. 24, 2020

(87) PCT Pub. No.: WO2018/205563
PCT Pub. Date: Nov. 15, 2018

(65) Prior Publication Data
US 2020/0224233 A1 Jul. 16, 2020

(30) Foreign Application Priority Data
May 12, 2017 (CN) .......................... 201710336026.7

(51) Int. Cl.
C12P 17/12 (2006.01)
C12N 15/77 (2006.01)
C12N 1/20 (2006.01)
C12R 1/15 (2006.01)

(52) U.S. Cl.
CPC .............. *C12P 17/12* (2013.01); *C12N 15/77* (2013.01); *C12N 1/205* (2021.05); *C12R 2001/15* (2021.05); *C12Y 207/02004* (2013.01); *C12Y 403/03007* (2015.07)

(58) Field of Classification Search
None
See application file for complete search history.

(56) References Cited

FOREIGN PATENT DOCUMENTS

| CN | 101250548 A | 8/2008 |
| CN | 101698845 A | 4/2010 |
| CN | 105018403 A | 11/2015 |
| CN | 107142234 A | 9/2017 |
| EP | 2374873 A1 | 10/2011 |

OTHER PUBLICATIONS

Perez-Garcia et al. (J of Biotechnol., vol. 258, 2017, pp. 59-68).*
Becker, J. et al., "Systems Metabolic Engineering of Corynebacterium Glutamicum for Production of the Chemical Chaperone Ectoine", Microbial Cell Factories, Nov. 15, 2013 (Nov. 15, 2013), 12 (110), pp. 1-15.
Schafer, R.A., "Improvement of Corynebacterium Glutamicum for Production of Lysine and Ectoine from Industrial Raw Materials", Dissertation, Dec. 31, 2016 (Dec. 31, 2016), pp. 1-120.
Chen, Then et al., "Deregulation of Feedback Inhibition of Phosphoenolpyruvate Carboxylase for Improved Lysine Production in Corynebacterium Glutamicum", Applied and Environmental Microbiology, Dec. 13, 2013 (Dec. 13, 2013), 80(4), pp. 1388-1393.
Chen, Then et al., "Coevolutionary Analysis Enabled Rational Deregulation of Allosteric Enzyme Inhibition in Corynebacterium Glutamicum for Lysine Production", Applied and Environmental Microbiology, Apr. 29, 2011 (Apr. 29, 2011), 77(13), pp. 4352-4360.
International Search Report for PCT Application PCT/CN2017/113806, dated Jan. 18, 2018, 6 pages.
Zhang, H., et al., "Metabolic Engineering of *Escherichia coli* for Ectoine Producti9on with the Fermentation Strategy of Supplementing Amino Donor", (Aug. 10, 2020) DOI: 10.21203/rs.3.rs-51701/v1 (pp. 1-17).
Perez-Garcia, F., et al, "Improved Fermentative Production of the Compatible Solute Ectoine by Cornebacterium Glutamicum from Glucose and Alternative Carbon Sources", (Sep. 20, 2017) 258: 59-68.
Chen, Wei et al., "Design of an Ectoine-responsive AraC Mutant and its Application in Metabolic Engineering of Ectoine Blosynthesis", Metabolic Engineering (2015) 30: 149-155.

* cited by examiner

*Primary Examiner* — Hope A Robinson
(74) *Attorney, Agent, or Firm* — Denise L. Mayfield; Dykema Gossett PLLC

(57) ABSTRACT

A method for producing ectoine by fermenting recombinant *Corynebacterium glutamicum*. The recombinant *Corynebacterium glutamicum* is obtained by overexpressing, in *Corynebacterium glutamicum*, an aspartokinase gene lysC of which feedback inhibition is relieved, then replacing the promoter of the dihydrodipicolinate synthase in the recombinant bacterium to attenuate the activity of the dihydropyrimidine dicarboxylic acid synthase, and then transforming the recombinant bacterium with the ectoine synthetic path related gene ectABC. The recombinant *Corynebacterium glutamicum* can be fermented using different cheap raw materials under a low salt condition to produce ectoine, and use cheap corn slurry instead of expensive yeast powder as a nutritional component, so as to further reduce the costs of the raw materials. In addition, the recombinant *Corynebacterium glutamicum* solves the biosafety problem, simplifies the post-extraction process, and has a good market application prospect.

9 Claims, 1 Drawing Sheet
Specification includes a Sequence Listing.

US 11,512,333 B2

METHOD FOR PRODUCING TETRAHYDROPYRIMIDINE BY FERMENTING RECOMBINANT CORYNEBACTERIUM GLUTAMICUM

CROSS-REFERENCE TO RELATED APPLICATIONS

This application is a United States national stage entry application of PCT/CN2017/113806, filed Nov. 30, 2017, to which priority is claimed.

TECHNICAL FIELD

The present invention belongs to the field of genetic engineering and biological fermentation technology, and in particular, to a method of producing ectoine by fermentation using a food safety grade microorganism, a recombinant *Corynebacterium glutamicum*.

BACKGROUND ART 1,4,5,6-tetrahydro-2-methyl-4-pyrimidinecarboxylic acid (Ectoine) is a cyclic amino acid derivative, and a compatible solute produced in cell by many salt-tolerant microorganisms to maintain osmotic pressure balance. It is important for stress tolerance of cell/enzyme, and can alleviate the adverse effects of hypertonic, high temperature, freeze-thaw, dryness, radiation and chemical reagents on proteins, nucleic acids, biofilms and whole cells. Therefore, ectoine has been widely used in the fields of cosmetics, medicines and enzyme preparations, and has broad market prospects.

At present, ectoine is mainly produced by the high-density fermentation of a halophilic microorganism, in particular *Halomonas*. This process is carried out by means of a method called "bacterial milking", including the steps of culturing cells under a high osmotic pressure and accumulating ectoine in the cells, and then stimulating ectoine to be released to the outside of the cells by a hypotonic shock, and then repeating hypertonic culture and hypotonic shock to obtain a higher concentration of ectoine. This process is complicated and requires cultivation under a high salt condition, which imposes high requirements for apparatuses, resulting in a very high production price.

With glucose or aspartic acid as a substrate, some processes currently being developed use a recombinant *E. coli* for fermentation under a low salt condition to obtain a higher concentration of ectoine, which simplifies the production process of ectoine. However, *E. coli* secretes endotoxins, and ectoine is mainly applied in the fields of cosmetics and medicine, so the endotoxins need to be removed, making the entire separation process complicated and increasing production cost. Therefore, it is very valuable to develop a safe and efficient recombinant microorganism which can be used to produce ectoine continuously under a low salt condition without secretion of endocrine.

SUMMARY OF THE INVENTION

The object of the present invention is to provide a method of producing ectoine by fermentation of a recombinant *Corynebacterium glutamicum* with high biosafety, high yield, simple operation and low cost, so as to overcome the defects in the prior art.

The biosynthesis pathway of ectoine is shown in FIG. 1. The main modification protocol of the present invention comprises: enhancing the carbon flow to the aspartic acid pathway by overexpressing the aspartokinase gene lysC of which the feedback inhibition is relieved (the gene sequence is set forth in SEQ ID NO: 1) in *Corynebacterium glutamicum*, wherein the gene contains a site-directed mutation Q298G and a strong promoter P1; decreasing the carbon flow to lysine by attenuating the activity of the dihydrodipicolinate synthase by replacing the promoter (its sequence is set forth in SEQ ID NO: 2) of the dihydrodipicolinate synthase gene; overexpressing the ectoine synthesis pathway-related gene ectABC (its sequence is set forth in SEQ ID NO: 1); and subjecting the strain to fermentation culture in a fermenter to obtain ectoine.

The invention firstly provides a recombinant *Corynebacterium glutamicum* containing a mutated lysC gene and promoter, a mutated dapA gene and promoter as well as an ectABC gene, wherein the sequence of the mutated lysC gene and promoter is set forth in SEQ ID NO: 1; the sequence of the mutated dapA gene and promoter is set forth in SEQ ID NO: 2; the sequence of the ectABC gene is set forth in SEQ ID NO: 3.

The recombinant *Corynebacterium glutamicum* of the present invention is prepared by the following method comprising:

(1) ligating the aspartokinase gene lysC of which the feedback inhibition is relieved and the strong promoter fragment P1 to a suicide plasmid to obtain a recombinant plasmid, and electro-transforming *Corynebacterium glutamicum* with the obtained recombinant plasmid to obtain a recombinant *C. glutamicum* lysC-P1-298;

(2) attenuating the expression of the dihydrodipicolinate synthase gene dapA in the recombinant *C. glutamicum* lysC-P1-298 by promoter replacement to obtain a recombinant *C. glutamicum* lysC-dap;

(3) transforming the recombinant *C. glutamicum* lysC-dap with an expression vector capable of overexpressing the ectoine synthesis pathway related gene ectABC to construct a recombinant *C. glutamicum* lysC-dap-ectABC.

In step (1), lysC1, lysC2, lysC3 and the strong promoter fragment P1 are ligated to a suicide plasmid, wherein the lysC1, lysC2, lysC3 are respectively obtained by PCR amplification with primer pairs of SEQ ID NOs: 5-6, SEQ ID NOs: 7-8 and SEQ ID NOs: 9-10 using the genome of *Corynebacterium glutamicum* as a template.

The strong promoter fragment P1 has the sequence as set forth in SEQ ID NO: 4, and the suicide plasmid is pK18mobsacB.

In step (2), a recombinant plasmid is obtained by ligating dap1 and dap2 fragments to a suicide plasmid.

The dap1 and dap2 fragments are respectively obtained by PCR amplification with primer pairs of SEQ ID NOs: 11-12 and SEQ ID NOs: 13-14 using the genome of *Corynebacterium glutamicum* as a template;

In step (3), the ectABC gene is ligated to the expression vector pXMJ19 to obtain a recombinant plasmid named as pXMJ-ectABC, and the recombinant plasmid is electro-transformed into the recombinant *C. glutamicum* lysC-dap of the step (2). The ectABC gene is obtained by PCR amplification with the primer pair of SEQ ID NOs: 15-16 using the genome of *Halomonas elongata* DSM2581 (purchased from the DSMZ) as a template.

The culture medium of the recombinant *Corynebacterium glutamicum* of the present invention contains chloramphenicol, in particular 5 mg/L of chloramphenicol.

The invention provides use of the recombinant strain *C. glutamicum* lysC-dap-ectABC in the production of ectoine.

The invention provides a method of producing ectoine by fermentation of the claimed recombinant *C. glutamicum* lysC-dap-ectABC, wherein the fermentation is performed by using a fermentable sugar-containing feedstock as a substrate, inoculating the recombinant C. glutamicum lysC-dap-ectABC, and at a fermentation temperature of 28-40° C., a pH of 5-8, and a dissolved oxygen value of 10%.

The fermentable sugar-containing feedstock is selected from the group consisting of molasses, sucrose, glucose, starch hydrolyzate, corn syrup, xylose, mannose and glycerin. The fermentation temperature is between 32 and 35° C. The pH is between 6 and 7. IPTG is added to a final concentration of 0.01-1 mM in 3 to 5 hours after fermentation.

A carbon source is fed during the fermentation, and the fermentation culture medium contains thiamine and biotin.

Corynebacterium glutamicum is a food safety grade microorganism widely used in the production of amino acids such as glutamate and lysine. Corynebacterium glutamicum does not secrete endotoxins, so employing Corynebacterium glutamicum to produce ectoine by fermentation solves the biosafety problem and greatly simplifies the post-extraction process. The recombinant Corynebacterium glutamicum constructed by the present invention can continuously produce by fermentation ectoine under a low salt condition by using inexpensive feedstocks such as glucose, which greatly simplifies the fermentation process of ectoine. Also, Corynebacterium glutamicum can be fermented by using various cheap feedstocks, such as waste molasses, sucrose, starch hydrolysate, etc., and also use cheap corn syrup instead of expensive yeast extract as a nutrient, so as to further reduce the cost of feedstock. Furthermore, the recombinant Corynebacterium glutamicum of the invention solves the biosafety problem, simplifies the post-extraction process, and has good market application prospects.

DETAILED DESCRIPTION OF THE INVENTION

Figure 1:
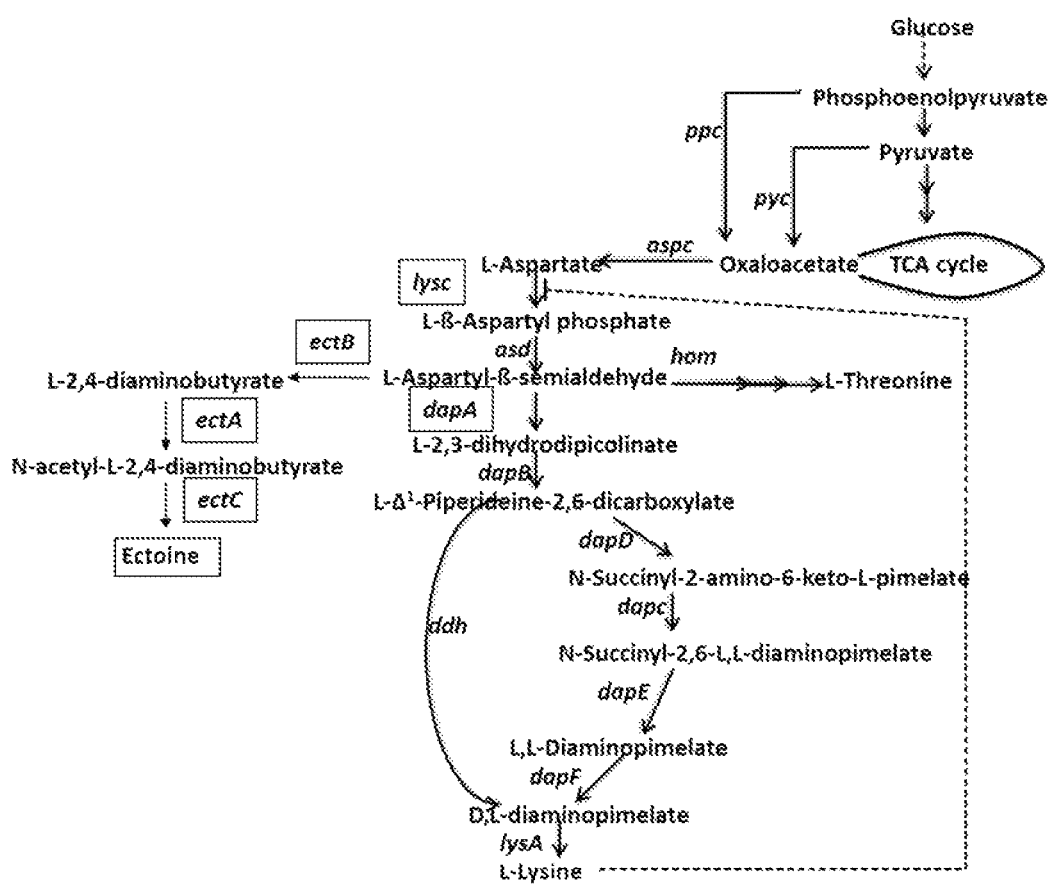
FIG. 1 shows the biosynthesis pathway of ectoine and a major modification site of the invention.

The following embodiments are intended to illustrate the invention, but are not intended to limit the scope of the invention. Modifications or replacements to the methods, steps or conditions of the invention without departing from the spirit and essence of the invention are intended to be included within the scope of the invention.

Unless otherwise specified, the chemical reagents used in the examples are conventional commercially available reagents, and the technical means used in the examples are conventional means well known to those skilled in the art.

Example 1: Overexpression of the Aspartokinase Gene lysC with Feedback Inhibition Relieved The direct synthesis precursor of ectoine is aspartate, and the first enzyme, aspartokinase, in the synthesis pathway of aspartate to ectoine is feedback inhibited by lysine and threonine. Therefore, the present invention first relieved the feedback inhibition to the enzyme by lysine and threonine via introducing a site-directed mutation Q298G into the aspartokinase gene, and a strong promoter P1 was inserted before the gene (lysC) (the sequence is: 5'-ggtgcacaaagCAAAAGCTGGGTACCTC-TATCTGGTGCCCTAAACGGGGGAATATTAAC GGGCCCAGGGTGGTCGCACCTTGGTTGGTAG-GAGTAGCATGGGATCC-3') (SEQ ID NO: 4) to enhance the expression of the gene. The specific process is as follows:

PCR was performed by using the genome of Corynebacterium glutamicum MB001 (Baumgart M et al, Appl Environ Microbiol 79: 6006-15 (2013)) as a template and the primers lysC-1-F (aggaaacagctatgacatgattacgtttcgcccagaac-caagtagcc) SEQ ID NO: 5 and lysC-1-R (CCCAGCTTTTGctttgtgcacctttcgatctacgt) SEQ ID NO: 6, to obtain about 1.0 kb of the gene fragment lysC1 and the PCR product was purified. PCR was performed by using the genome of Corynebacterium glutamicum MB001 as a template and the primers lysC-2-F (CATGGGATC-Catggccctggtcgtacagaa) SEQ ID NO: 7 and lysC-2-R (ga-gacgttgcccagaaccatgtcaat gttgatttctgca) SEQ ID NO: 8, to obtain about 0.9 kb of the gene fragment lysC2 and the PCR product was purified. PCR was performed by using the genome of Corynebacterium glutamicum MB001 as a template and the primers lysC-3-F (acatggttctgggcaacgtctcttctgtagaagacg) SEQ ID NO: 9 and lysC-3-R (tgcatgcctgcaggtcgactacataaggtccgacatcgcct) SEQ ID NO: 10, to obtain about 1.0 kb of the gene fragment lysC3 and the PCR product was purified. PCR was performed by using the plasmid pEC-yqhD-pduCDEGH constructed in our lab (Huang et al., Scientific Reports 7: 42246, 2017) as a template and the primers P1-F (ggtgcacaaagCAAAAGCTGGG TACCTCTATCTGGT) SEQ ID NO: 17 and P1-R (ccagggccatGGATCCCATGC-TACTCCT) SEQ ID NO: 18, to obtain about 0.1 kb of the gene fragment P1 and the PCR product was purified. Corynebacterium glutamicum suicide plasmid pK18mobsacB (Journal of Biotechnology 104 (2003) 287-299) was digested with two enzymes EcoRI/XbaI, and the lysC1, lysC2, lysC3_and P1 fragments were ligated into pK18mobsacB by Gibson Assembly kit (NEB). The obtained recombinant plasmid was named as pK18-lysC. The pK18-lysC was electro-transformed Corynebacterium glutamicum MB001 using an electroporation instrument (Bole). The electric shock was at a voltage of 2.5 KV, a resistance of 200Ω, a capacitance of 25 μF (width of the electric shock cuvette is 2 mm). A recombinant strain was obtained through two screenings, one of which was on a LB plate containing 25 mg/L of kanamycin. The recombinant strain was further cultured overnight in a liquid LB culture medium, followed by a second screening on a LB plate containing 100 g/L of sucrose. Colony PCR was carried out with the primers P1-1-F and lysC-3-R, and a fragment of about 2 Kb could be cloned from the correct recombinant, which was named as C. glutamicum lysC-P1-298. A key feature of the recombinant strain is that it comprises a mutated lysC gene and promoter, as set forth in SEQ ID NO: 1, which contains a site-directed mutation Q298G at bases 998-1000 of the nucleic acid sequence. The recombinant strain can produce 18 g/L of lysine using 80 g/L of glucose, while the wild strain MB001 cannot produce lysine, indicating that in this example, the lysC gene was successfully modified, that is, glucose can flow to a metabolic branch common to lysine and ectoine. The specific fermentation process refers to the example 4.

Example 2: Attenuating the Expression of Dihydrodipicolinate Synthase Gene dapA by Promoter Replacement Since the main fermentation product of the recombinant strain C. glutamicum lysC-P1-298 is lysine, in order to allow more substrates to be used in the synthesis of ectoine, the expression of the dihydrodipicolinate synthase gene dapA was further attenuated. PCR was performed by using the genome of *Corynebacterium glutamicum* MB001 as a template and the primers dap-1-F (ctatgacatgattacgaattcagatggttttcctgaccagctt) SEQ ID NO: 11 and dap-1-R (gggaagaaggaaaccttgaactctatgagcacagg) SEQ ID NO: 12, to obtain about 1.0 kb of the gene fragment dap1 and the PCR product was purified. PCR was performed by using the genome of *Corynebacterium glutamicum* MB001 as a template and the primers dap-2-F (ttcaaggtttccttcttccctcat-ttggggg) SEQ ID NO: 13 and dap-2-R (tgcctgcaggtcgactctagaggcct gtaaaggctcatttcag) SEQ ID NO: 14 to obtain about 1.0 kb of the gene fragment dap2 and the PCR product was purified. The *Corynebacterium glutamicum* suicide plasmid pK18mobsacB was digested with two enzymes EcoRI/XbaI, and the dap1 and dap2 fragments were ligated into the pK18mobsacB by Gibson Assembly kit (NEB). The obtained recombinant plasmid was named as pK18-dap. The pK18-dap was electro-transformed the *C. glutamicum* lysC-P1-298 using an electroporation instrument (Bole). The electric shock was at a voltage of 2.5 KV, a resistance of 200Ω, a capacitance of 25 μF (width of the electric shock cuvette is 2 mm). A recombinant strain was obtained through two screenings, in one of which the recombinant strain was screened on a LB plate containing 25 mg/L of kanamycin. The recombinant strain was further cultured overnight in a liquid LB culture medium, followed by a second screening on a LB plate containing 100 g/L of sucrose. Colony PCR was performed using the primers dap-1-F and dap-2-R and the sequencing was performed, and the correct recombinant strain was named as *C. glutamicum* lysC-dap. A key feature of the recombinant strain is that it includes a mutated dapA gene and promoter, whose sequence is set forth in SEQ ID NO: 2. The recombinant strain can produce 6 g/L of lysine and 2 g/L of glycine using 80 g/L of glucose. The specific fermentation process refers to the example 4.

Example 3: Overexpression of the Ectoine Synthesis Pathway Related Gene ectABC

To enhance the expression of the key gene in the ectoine synthesis pathway, the ectABC gene was artificially synthesized, whose sequence is set forth in SEQ ID NO: 3. PCR was performed on the genome of *Halomonas elongata* DSM 2581 with the primers ectABC-F (tgcatgcctgcaggtcgactAG-GAGGCCCTTCAGatgaacg) SEQ ID NO: 15 and ect-ABC-R (ccgccaaaacagccaagctgttacagcggcttctggtcgt) SEQ ID NO: 16, to obtain about 2.5 kb of the gene fragment ectABC and the PCR product was purified. The *Corynebacterium glutamicum* expression plasmid pXMJ19 (purchased from addgene) was digested with two enzymes EcoRI/XbaI, and the ectABCfragment was further ligated into the pXMJ19 by Gibson Assembly kit (NEB). The obtained recombinant plasmid was named as pXMJ-ectABC.

The pXMJ-ectABC was electro-transformed the *C. glutamicum* lysC-dap using an electroporation instrument (Bole). The electric shock was at a voltage of 2.5 KV, a resistance of 200Ω, a capacitance of 25 μF (width of the electric shock cup is 2 mm). A recombinant strain was screened on a LB plate containing 5 mg/L of chloramphenicol, which was named as *C. glutamicum* lysC-dap-ectABC. A key feature of the recombinant strain is that it includes ectABC gene, whose sequence is set forth in SEQ ID NO: 3. The recombinant strain can produce 12 g/L of ectoine by using 80 g/L of glucose, while none of the strains in examples 1 and 2 can produce ectoine. The specific fermentation process refers to the example 4.

Example 4: Fermentation of the Recombinant *C. glutamicum* lysC-Dap-ectABC

The wild type strain *Corynebacterium glutamicum* MB001 and recombinant strain *C. glutamicum* lysC-P1-298, *C. glutamicum* lysC-dap, *C. glutamicum* lysC-dap-ectABC were cultured overnight on LB plates. Single colonies from these fresh plates were inoculated into 250 ml baffled shake flasks containing 30 ml seed medium, and cultured at 32° C., 200 rpm for 12 hours.

The formulation of the seed medium comprises (g/L): glucose 40, $(NH_4)_2SO_4$ 5.0, K2HPO4 1.5, MgSO4 1.0, MnSO4 0.005, FeSO4 0.005, corn syrup 30. The culture medium of the *C. glutamicum* lysC-dap-ectABC was additionally added with 5 mg/L of chloramphenicol.

The seed solution was inoculated into 2 L fermentation medium in an inoculation amount of 10%, and the fermentation was carried out in a 5 L fermenter. The temperature was controlled to be 320° C., the aeration rate was 1 vvm, and the rotation speed was adjusted to keep the dissolved oxygen level above 10%. The pH was controlled by feeding ammonia to be at about 7.0.

The formulation of the fermentation medium comprises (g/L): glucose 80, $(NH_4)_2SO_4$ 30.0, K2HPO4 2.5, MgSO4 1.0, MnSO4 0.010, FeSO4 0.010, corn syrup 15, biotin 0.0005, and thiamine hydrochloride 0.005. The culture medium of the *C. glutamicum* lysC-dap-ectABC was additionally added with 5 mg/L of chloramphenicol, and 1 mM IPTG was added in 3 hours after fermentation.

The fermentation was carried out for 72 hours, and the product concentration was determined by liquid chromatography. The wild strain MB001 did not produce amino acids or ectoine, and the recombinant strain *C. glutamicum* lysC-P1-298 obtained in the example 1 produced 18 g/L of lysine but did not produce ectoine. The recombinant strain *C. glutamicum* lysC-dap obtained in the example 2 produced 6 g/L of lysine and 2 g/L of glycine but did not produce ectoine. The recombinant strain *C. glutamicum* lysC-dap-ectABC obtained in the example 3 produced 2 g/L of lysine and 12 g/L of ectoine.

It can be seen that, based on examples 1 and 2 of the present application, the further constructed recombinant strain *C. glutamicum* lysC-dap-ectABC can ferment substrate to produce ectoine, and the amount of the produced ectoine is at the same level compared with other strains in the prior art. Since the recombinant strain *C. glutamicum* lysC-dap-ectABC of the present invention is food-safe and does not produce endotoxins, the cumbersome steps in the subsequent engineering for removing endotoxins and isolating and purifying the products are not necessary, which not only improves the safety of the product, but also greatly reduces the production cost.

Although the present invention has been described in detail by the general description and the concrete embodiments, certain modification and amendments can be made based on the present invention, which will be apparent to those skilled in the art. Therefore, such modifications or amendments made without departing from the spirit of the invention are intended to be included within the patentable scope of the invention.

The invention claimed is:

1. A recombinant *Corynebacterium glutamicum* (*C. glutamicum*), comprising a mutated lysC gene and promoter, a mutated dihydropicolinate synthase (dapA) gene and promoter, and an ectoine synthesis pathway related gene (ectABC),
wherein the mutated lysC gene and promoter has the nucleotide sequence of SEQ ID NO: 1;
the mutated dapA gene and promoter has the nucleotide sequence of SEQ ID NO: 2; and
the ectABC gene has the nucleotide sequence of SEQ ID NO: 3, and wherein the recombinant *C. glutamicum* over expresses the lysC gene and the ectABC gene.

2. The recombinant *C. glutamicum* of claim 1, prepared by:
(1) ligating the lysC gene, wherein feedback inhibition is relieved and a strong promoter fragment P1 to a suicide plasmid, to obtain a recombinant plasmid and electro-transforming the *C. glutamicum* with the recombinant plasmid to obtain a recombinant bacterium *C. glutamicum* lysC-P1-298;
(2) attenuating the expression of the dapA gene in the recombinant *C. glutamicum* lysC-P1-298 by promoter replacement to obtain a recombinant *C. glutamicum* lysC-dap; and
(3) transforming the recombinant *C. glutamicum* lysC-dap with an expression vector overexpressing the ectABC gene, to construct a recombinant *C. glutamicum* lysC-dap-ectABC.

3. The recombinant *C. glutamicum* of claim 2, wherein in step (1), the lysC gene and the strong promoter fragment P1 are ligated to the suicide plasmid, and wherein the lysC gene is a lysC1, lysC2 or lysC3 obtained by PCR amplification and using the genome of *C. glutamicum* as a template.

4. The recombinant *C. glutamicum* of claim 2, wherein the strong promoter fragment P1 has a nucleotide sequence of SEQ ID NO: 4, and the suicide plasmid is pK18mobsacB.

5. The recombinant *C. glutamicum* of claim 2 further comprising ligating the ectABC gene to an expression vector pXMJ19 to obtain a recombinant plasmid pXMJ-ectABC, and the recombinant plasmid is electro-transformed into the recombinant *C. glutamicum* lysC-dap of step (2), wherein the ectABC gene is obtained by PCR amplification and using the genome of *Halomonas elongata* DSM 2581 as a template.

6. A medium comprising the recombinant *C. glutamicum* of claim 1, wherein the medium further comprises chloramphenicol.

7. A method for producing ectoine by fermentation of the recombinant *C. glutamicum* of claim 1, comprising:
providing a fermentable sugar-containing feedstock as a substrate;
inoculating the recombinant *C. glutamicum*; and
fermenting at a temperature of 28-40° C., a pH of 5-8 and a dissolved oxygen value of 10%, thereby producing ectoine.

8. The method of claim 7, wherein the fermentable sugar-containing feedstock is selected from the group consisting of molasses, sucrose, glucose, starch hydrolyzate, corn syrup, xylose, mannose and glycerin; and the fermentation temperature is between 32 and 35° C., the pH is between 6 and 7, and isopropyl β-D-1-thiogalactopyranoside (IPTG) is added at a final concentration of 0.01-1 mM 3-5 hours after fermentation.

9. The method of claim 7, wherein a carbon source is fed during the fermentation, and the fermentation medium contains thiamine and biotin.

* * * * *

SEQUENCE LISTING

<160> NUMBER OF SEQ ID NOS: 18

<210> SEQ ID NO 1
<211> LENGTH: 1372
<212> TYPE: DNA
<213> ORGANISM: Artificial Sequence
<220> FEATURE:
<223> OTHER INFORMATION: Mutated LysC gene and promoter

<400> SEQUENCE: 1

| | | | | | |
|---|---|---|---|---|---|
| ggtgcacaaa | gcaaaagctg | ggtacctcta | tctggtgccc | taaacggggg | aatattaacg | 60 |
| ggcccagggt | ggtcgcacct | tggttggtag | gagtagcatg | ggatccatgg | ccctggtcgt | 120 |
| acagaaatat | ggcggttcct | cgcttgagag | tgcggaacgc | attagaaacg | tcgctgaacg | 180 |
| gatcgttgcc | accaagaagg | ctggaaatga | tgtcgtggtt | gtctgctccg | caatgggaga | 240 |
| caccacggat | gaacttctag | aacttgcagc | ggcagtgaat | cccgttccgc | cagctcgtga | 300 |
| aatggatatg | ctcctgactg | ctggtgagcg | tatttctaac | gctctcgtcg | ccatggctat | 360 |
| tgagtccctt | ggcgcagaag | cccaatcttt | cacgggctct | caggctggtg | tgctcaccac | 420 |
| cgagcgccac | ggaaacgcac | gcattgttga | tgtcactcca | ggtcgtgtgc | gtgaagcact | 480 |
| cgatgagggc | aagatctgca | ttgttgctgg | tttccagggt | gttaataaag | aaacccgcga | 540 |
| tgtcaccacg | ttgggtcgtg | gtggttctga | caccactgca | gttgcgttgg | cagctgcttt | 600 |
| gaacgctgat | gtgtgtgaga | tttactcgga | cgttgacggt | gtgtataccg | ctgacccgcg | 660 |
| catcgttcct | aatgcacaga | agctggaaaa | gctcagcttc | gaagaaatgc | tggaacttgc | 720 |
| tgctgttggc | tccaagattt | tggtgctgcg | cagtgttgaa | tacgctcgtg | cattcaatgt | 780 |
| gccacttcgc | gtacgctcgt | cttatagtaa | tgatcccggc | actttgattg | ccggctctat | 840 |
| ggaggatatt | cctgtggaag | aagcagtcct | taccggtgtc | gcaaccgaca | agtccgaagc | 900 |
| caaagtaacc | gttctgggta | tttccgataa | gccaggcgag | gctgcgaagg | ttttccgtgc | 960 |
| gttggctgat | gcagaaatca | acattgacat | ggttctgggc | aacgtctctt | ctgtagaaga | 1020 |
| cggcaccacc | gacatcacct | tcacctgccc | tcgttccgac | ggccgccgcg | cgatggagat | 1080 |
| cttgaagaag | cttcaggttc | agggcaactg | gaccaatgtg | ctttacgacg | accaggtcgg | 1140 |
| caaagtctcc | ctcgtgggtg | ctggcatgaa | gtctcaccca | ggtgttaccg | cagagttcat | 1200 |
| ggaagctctg | cgcgatgtca | acgtgaacat | cgaattgatt | tccacctctg | agattcgtat | 1260 |
| ttccgtgctg | atccgtgaag | atgatctgga | tgctgctgca | cgtgcattgc | atgagcagtt | 1320 |
| ccagctgggc | ggcgaagacg | aagccgtcgt | ttatgcaggc | accggacgct | aa | 1372 |

<210> SEQ ID NO 2
<211> LENGTH: 1105
<212> TYPE: DNA
<213> ORGANISM: Artificial Sequence
<220> FEATURE:
<223> OTHER INFORMATION: Mutated dapA gene and promoter

<400> SEQUENCE: 2

| | | | | | |
|---|---|---|---|---|---|
| gcaaagctca | cacccacgag | ctaaaaattc | atatagttaa | gacaacattt | ttggctgtaa | 60 |
| aagacagccg | taaaaacctc | ttgctcgtgt | caattgttct | tatcggaatg | tggcttgggc | 120 |
| gattgttatg | caaaagttgt | taggtttttt | gcggggttgt | ttaaccccca | aatgagggaa | 180 |
| gaaggaaacc | ttgaactcta | tgagcacagg | tttaacagct | aagaccggag | tagagcactt | 240 |
| cggcaccgtt | ggagtagcaa | tggttactcc | attcacggaa | tccggagaca | tcgatatcgc | 300 |
| tgctggccgc | gaagtcgcgg | cttatttggt | tgataagggc | ttggattctt | ggttctcgc | 360 |

```
gggcaccact ggtgaatccc aacgacaac cgccgctgaa aaactagaac tgctcaaggc    420
cgttcgtgag gaagttgggg atcgggcgaa gctcatcgcc ggtgtcggaa ccaacaacac    480
gcggacatct gtggaacttg cggaagctgc tgcttctgct ggcgcagacg gccttttagt    540
tgtaactcct tattactcca agccgagcca agagggattg ctggcgcact tcggtgcaat    600
tgctgcagca acagaggttc caatttgtct ctatgacatt cctggtcggt caggtattcc    660
aattgagtct gataccatga gacgcctgag tgaattacct acgattttgg cggtcaagga    720
cgccaagggt gacctcgttg cagccacgtc attgatcaaa gaaacgggac ttgcctggta    780
ttcaggcgat gacccactaa accttgtttg gcttgctttg ggcggatcag gtttcatttc    840
cgtaattgga catgcagccc ccacagcatt acgtgagttg tacacaagct cgaggaagg     900 cgacctcgtc cgtgcgcggg aaatcaacgc caaactatca ccgctggtag ctgcccaagg    960
tcgcttgggt ggagtcagct tggcaaaagc tgctctgcgt ctgcagggca tcaacgtagg   1020
agatcctcga cttccaatta tggctccaaa tgagcaggaa cttgaggctc tccgagaaga   1080
catgaaaaaa gctggagttc tataa                                         1105

<210> SEQ ID NO 3
<211> LENGTH: 2432
<212> TYPE: DNA
<213> ORGANISM: Halomonas elongata

<400> SEQUENCE: 3
atgaacgcaa ccacagagcc ctttacaccc tccgccgacc tggccaagcc cagcgtggcc     60
gatgccgtgg tcggccatga ggcctcaccg ctcttcatcc gcaagccaag ccccgatgac    120
ggctggggca tctacgagct ggtcaagtcc tgtccgcctc tcgacgtcaa ttccgcctac    180
gcctatctgt tgctggccac ccagttccgc gatagctgcg ccgtgcgac caacgaagag    240 ggcgagatcg tcggcttcgt ttccggctac gtgaagagca cgccccga tacctatttc     300 ctctggcagg ttgccgtggg cgagaaggca cgtggcaccg gctggcccg tcgtctggtg    360 gaagccgtga tgacacgccc ggaaatggcc gaggtccacc atctcgagac cactatcacg    420
cccgacaacc aggcgtcctg gggcttgttc cgccgtctcg ccgatcgctg gcaggcgccg    480
ttgaacagcc gcgaatactt ctccaccgat caactcggcg gtgagcatga cccggaaaac    540
ctcgttcgca tcggcccgtt ccagaccgac cagatctgag ccgggacgcc gcctggccgg    600
cccggtacgg gccggcaacc cgtctttcg ttttatcact ttccccaca ggaggtcgca    660 atgcagaccc agattctcga acgcatggag tccgacgttc ggacctactc ccgctccttc    720
ccggtcgtct tcaccaaggc gcgcaatgcc cgcctgaccg acgaggaagg cgcgagtac    780 atcgacttcc tggccggtgc cggcacctg aactacggcc acaacaaccc gcacctcaag    840
caggcgctgc tcgactatat cgacagcgac ggcatcgtcc acggcctgga cttctggact    900
gcggccaagc gcgactatct ggaaaccctg aagaggtga tcctcaagcc gcgcggtctc    960
gactacaagg tgcatctgcc cggaccgact ggcaccaacg ccgtcgaggc ggccattcgc   1020
ctggcccggg tcgccaaggg gcgccacaat atcgtctcct tcaccaacgg ctttcatggc   1080
gtcaccatgg gcgcgctggc gaccaccggt aaccgcaagt ccgcgaggc caccggtggc   1140 gtgccgaccc aggctgcttc cttcatgccg ttcgatggct acctcggcag cagcaccgac   1200
accctcgact acttcgagaa gctgctcggc gacaagtccg gcggcctgga cgtgcccgcg   1260
gcggtgatcg tcgagacagt gcagggcgag ggcggtatca atgtcgccgg cctggagtgg   1320
```

```
ctcaagcgcc tcgagagcat ctgccgcgcc aatgacatcc tgctgatcat cgacgacatc    1380
caggcgggct gcggccggac cggcaagttc ttcagcttcg agcatgccgg catcacgccg    1440
gatatcgtga ccaactccaa gtcgctgtcc ggttacggcc tgccgttcgc tcacgtcctg    1500 atgcgcccg agctcgacaa gtggaagccc ggtcagtaca acggcacctt ccgcggcttc     1560
aacctggctt tcgccactgc tgctgccgcc atgcgcaagt actggagcga cgacaccttc    1620
gagcgtgacg tgcagcgcaa ggctcgcatc gtcgaggaac gcttcggcaa gatcgccgcc    1680
tggctgagcg agaacggcat cgaggcctcc gagcgcggcc gcgggctgat gcggggcatc    1740
gacgtgggtt ccggcgatat cgccgacaag atcacccacc aagccttcga gaacgggttg    1800
atcatcgaaa ccagcggtca ggacggcgaa gtggtcaagt gcctgtgccc gctgaccatt    1860
cccgacgaag acctggtcga gggactcgac atcctcgaga ccagcaccaa gcaggccttt    1920
agctgatcgc ctgaggtgcg ccatcgggcc tgtccatggc atcctgtatc ggtcggccgt    1980
gcgcggccgg ccagtcattg attcactgga gaatcgacat gatcgttcgc aatctcgaag    2040
aagcgcgcca gaccgaccgt ctggtcaccg ccgaaaacgg caactgggac agcacccgcc    2100
tgtcgctggc cgaagatggt ggcaactgct ccttccacat caccgcatc ttcgagggta     2160 ccgagaccca catccactat aagcatcact tcgaggctgt ttattgcatc gaaggcgagg    2220
gcgaagtgga aaccctggcc gatggcaaga tctggcccat caagccgggt gacatctaca    2280
tcctcgacca gcacgacgag cacctgctgc gcgccagcaa gaccatgcac ctggcctgcg    2340
tgttcacgcc gggcctgacc ggcaacgaag tgcaccgcga agacggttcc tacgcacctg    2400
ccgacgaagc cgacgaccag aagccgctgt aa                                   2432

<210> SEQ ID NO 4
<211> LENGTH: 106
<212> TYPE: DNA
<213> ORGANISM: Artificial Sequence
<220> FEATURE:
<223> OTHER INFORMATION: P1

<400> SEQUENCE: 4
ggtgcacaaa gcaaaagctg ggtacctcta tctggtgccc taaacggggg aatattaacg    60
ggcccagggt ggtcgcacct tggttggtag gagtagcatg ggatcc                   106

<210> SEQ ID NO 5
<211> LENGTH: 47
<212> TYPE: DNA
<213> ORGANISM: Artificial Sequence
<220> FEATURE:
<223> OTHER INFORMATION: lysC-1-F

<400> SEQUENCE: 5
aggaaacagc tatgacatga ttacgtttcg cccagaacca agtagcc                  47

<210> SEQ ID NO 6
<211> LENGTH: 35
<212> TYPE: DNA
<213> ORGANISM: Artificial Sequence
<220> FEATURE:
<223> OTHER INFORMATION: lysC-1-R

<400> SEQUENCE: 6
cccagctttt gctttgtgca cctttcgatc tacgt                               35

<210> SEQ ID NO 7
<211> LENGTH: 30
```

```
<212> TYPE: DNA
<213> ORGANISM: Artificial Sequence
<220> FEATURE:
<223> OTHER INFORMATION: lysC-2-F

<400> SEQUENCE: 7
catgggatcc atggccctgg tcgtacagaa                                    30

<210> SEQ ID NO 8
<211> LENGTH: 39
<212> TYPE: DNA
<213> ORGANISM: Artificial Sequence
<220> FEATURE:
<223> OTHER INFORMATION: lysC-2-R

<400> SEQUENCE: 8
gagacgttgc ccagaaccat gtcaatgttg atttctgca                          39

<210> SEQ ID NO 9
<211> LENGTH: 36
<212> TYPE: DNA
<213> ORGANISM: Artificial Sequence
<220> FEATURE:
<223> OTHER INFORMATION: lysC-3-F

<400> SEQUENCE: 9
acatggttct gggcaacgtc tcttctgtag aagacg                             36

<210> SEQ ID NO 10
<211> LENGTH: 41
<212> TYPE: DNA
<213> ORGANISM: Artificial Sequence
<220> FEATURE:
<223> OTHER INFORMATION: lysC-3-R

<400> SEQUENCE: 10
tgcatgcctg caggtcgact acataaggtc cgacatcgcc t                       41

<210> SEQ ID NO 11
<211> LENGTH: 43
<212> TYPE: DNA
<213> ORGANISM: Artificial Sequence
<220> FEATURE:
<223> OTHER INFORMATION: dap-1-F

<400> SEQUENCE: 11
ctatgacatg attacgaatt cagatggttt tcctgaccag ctt                     43

<210> SEQ ID NO 12
<211> LENGTH: 35
<212> TYPE: DNA
<213> ORGANISM: Artificial Sequence
<220> FEATURE:
<223> OTHER INFORMATION: dap-1-R

<400> SEQUENCE: 12
gggaagaagg aaaccttgaa ctctatgagc acagg                              35

<210> SEQ ID NO 13
<211> LENGTH: 31
<212> TYPE: DNA
<213> ORGANISM: Artificial Sequence
<220> FEATURE:
<223> OTHER INFORMATION: dap-2-F

<400> SEQUENCE: 13
```

```
ttcaaggttt ccttcttccc tcatttgggg g                           31
```

<210> SEQ ID NO 14
<211> LENGTH: 43
<212> TYPE: DNA
<213> ORGANISM: Artificial Sequence
<220> FEATURE:
<223> OTHER INFORMATION: dap-2-R

<400> SEQUENCE: 14

```
tgcctgcagg tcgactctag aggcctgtaa aggctcattt cag              43
```

<210> SEQ ID NO 15
<211> LENGTH: 41
<212> TYPE: DNA
<213> ORGANISM: Artificial Sequence
<220> FEATURE:
<223> OTHER INFORMATION: ectABC-F

<400> SEQUENCE: 15

```
tgcatgcctg caggtcgact aggaggccct tcagatgaac g                41
```

<210> SEQ ID NO 16
<211> LENGTH: 40
<212> TYPE: DNA
<213> ORGANISM: Artificial Sequence
<220> FEATURE:
<223> OTHER INFORMATION: ectABC-R

<400> SEQUENCE: 16

```
ccgccaaaac agccaagctg ttacagcggc ttctggtcgt                  40
```

<210> SEQ ID NO 17
<211> LENGTH: 36
<212> TYPE: DNA
<213> ORGANISM: Artificial Sequence
<220> FEATURE:
<223> OTHER INFORMATION: P1-F

<400> SEQUENCE: 17

```
ggtgcacaaa gcaaaagctg ggtacctcta tctggt                      36
```

<210> SEQ ID NO 18
<211> LENGTH: 28
<212> TYPE: DNA
<213> ORGANISM: Artificial Sequence
<220> FEATURE:
<223> OTHER INFORMATION: P1-R

<400> SEQUENCE: 18

```
ccagggccat ggatcccatg ctactcct                               28
```